(12) United States Patent
Khalid et al.

(10) Patent No.: US 8,653,478 B2
(45) Date of Patent: Feb. 18, 2014

(54) METHOD AND APPARATUS FOR ENHANCED PATHOGEN MORTALITY IN VENTILATION SYSTEMS USING SOLID STATE MEANS OF GENERATION OF UVC

(71) Applicant: Najeeb Ashraf Khalid, Westmount (CA)

(72) Inventors: Najeeb Ashraf Khalid, Westmount (CA); Alexander Novikov, Hampstead (CA)

(73) Assignee: Najeeb Ashraf KHALID, Westmount, QC, CA (US)

( * ) Notice: Subject to any disclaimer, the term of this patent is extended or adjusted under 35 U.S.C. 154(b) by 0 days.

(21) Appl. No.: 13/732,684

(22) Filed: Jan. 2, 2013

(65) Prior Publication Data

US 2013/0221235 A1    Aug. 29, 2013

Related U.S. Application Data

(60) Provisional application No. 61/582,700, filed on Jan. 3, 2012.

(51) Int. Cl.
*A61L 2/00* (2006.01)

(52) U.S. Cl.
CPC ........................... *A61L 2/00* (2013.01)
USPC .................. 250/455.11; 250/436; 422/22

(58) Field of Classification Search
USPC ........... 250/455.11, 432 R, 435, 436; 422/22, 422/24
See application file for complete search history.

(56) References Cited

U.S. PATENT DOCUMENTS

| | | | |
|---|---|---|---|
| 3,347,025 A | 10/1967 | Wiley | |
| 5,616,172 A | 4/1997 | Tuckerman et al. | |
| 5,656,242 A | 8/1997 | Morrow et al. | |
| 6,555,011 B1 | 4/2003 | Tribelsky et al. | |
| 7,407,633 B2 | 8/2008 | Potember et al. | |
| 2005/0249630 A1 | 11/2005 | Odumuye et al. | |
| 2010/0320440 A1 | 12/2010 | Khan | |
| 2011/0142725 A1 | 6/2011 | Liu et al. | |
| 2013/0015362 A1* | 1/2013 | Hooper et al. | 250/372 |

* cited by examiner

*Primary Examiner* — Kiet T Nguyen
(74) *Attorney, Agent, or Firm* — Anglehart et al.

(57) ABSTRACT

A novel method and apparatus is presented wherein an output of infra-red solid state laser or multiple of such lasers is quadrupled in frequency to obtain a laser output that emits energy in ultra violet C spectrum, and wherein this energy is then provided within an air duct as is normal in HVAC systems so as it kill pathogens that are airborne and being carried through the conduit. Further such a method reduces production of ozone, detrimental to human health and produced in other means of generating UVC and provides ease of control of such energy so as to maintain the required energy at a steady level for prolonged period of time.

9 Claims, 3 Drawing Sheets

METHOD AND APPARATUS FOR ENHANCED PATHOGEN MORTALITY IN VENTILATION SYSTEMS USING SOLID STATE MEANS OF GENERATION OF UVC

TECHNICAL FIELD

The present application relates to ventilation systems. The present application also relates to pathogen control using UVC.

BACKGROUND

The knowledge that electromagnetic radiation with wavelengths in the Ultra Violet C band (210 nm to 280 nm) kills bacteria is well established with the first recognition of this discovery resulting in a Nobel prize awarded to Niels Ryberg Finsen for Physiology or Medicine in 1903. It is now known that DNA of living organisms is highly absorbent at 260 nm.

Pathogens are a serious issue in hospitals, killing over 100,000 persons per year in the USA. Pathogens are spread from infected individuals through touch and through the air. Removal of pathogens is very difficult. Filtration is commonly used but does not remove the pathogen; filtration makes matters worse by providing sites for the pathogens to multiply as filtration does not kill them. UVC using mercury and fluorescent lamps have been used but cost, production of ozone, maintenance and heat are barriers to large scale adoption.

Life on this planet evolved in the absence of UVC, specifically 260 nm wavelength of light. The ozone layers shields the planet form this wavelength of electro-magnetic radiation. All life forms are extremely sensitive to this wavelength and cells are destroyed with small doses of this radiation. In simple organisms, this means immediate death, in complex organisms, it means various cancers and cellular destruction leading to death.

The first attempts in removing pathogens from the air were to filter them out as disclosed by M. WILEY et al in U.S. Pat. No. 3,347,025. Filters at that time were not fine enough to be helpful as well as the pathogens were not killed. Filters do block bacteria but not all pathogens as well as the filter surfaces become sites for the pathogens to grow in numbers.

Attempts with varying levels of success have been made to use UVC to kill pathogens to date.

Traditionally UVC is created through the mercury arc lamps and through gas discharge tubes. These sources produce a complex spectrum of electromagnetic radiation and some of it is in the UVC region and a smaller part of this UVC is exactly in the region that is of interest in killing pathogens.

The production of UVC by above means also produces ozone as a side effect of the use of high strength electromagnetic field necessary to operate the lamps. In this application ozone has to be removed as it is has a negative impact on human health. This adds to the cost and the complexity of the equipment.

An alternative method of removing pathogens from the air is to use HEPA filters as disclosed by Mark A. Tuckerman et al in U.S. Pat. No. 5,616,172. This method has a draw back as the pathogens are not killed but blocked and the filter surfaces are used by the pathogen to multiply. Periodic replacement of the filters can solve this but at a cost of very frequent maintenance. Smaller pathogens, like viruses, cannot be removed by this method.

Further improvement on this filter based method has been disclosed by William Morrow et al in U.S. Pat. No. 5,656,242, where UVC produced from tube lights is used to kill the pathogen that is deposited on the filter surfaces. Although an improvement, the method requires a large number of tube lights, regular replacement of these tube lights as they have rapidly declining power curve with time and they need to be operating twenty four hours a day and very day.

Another method found in U.S. Pat. No. 7,407,633 uses UV light to create ozone to kill pathogens. While effective in killing most forms of bacteria, ozone still needs to be removed.

US Pre-Grant Patent Application Publication (PG-Pub) 2005/0249630 A1 by Olubunmi Ayodele Odumuye et al discloses a method wherein UV light produced by tube lights is used to purify the air or other carriers of pathogens such as water. This method suffers from the drawbacks of all of the above methods, namely it is costly and produces ozone.

US PG-Pub 2010/0320440 A1 teaches producing electromagnetic radiation in UVC, specifically 365 nm, aimed at killing pathogens. This method is effective provided there is sufficient time to overcome the low power of these devices and is confined to purifying water in small containers over hours.

In U.S. Pat. No. 6,555,011 by Zamir Tribelsky et al, claim is made of an apparatus whereby the gas or liquid to be disinfected is contained in a parabolic chamber that is then exposed to electromagnetic radiation of many types, the claim is broad without specific information on how to implement such a solution using lasers and claim is confined to use in a parabolic chamber.

US PG-Pub 2011/0142725 A1 by Xuanbin Liu et al discloses an air purification method that uses electromagnetic radiation through a glass with a coating of a photo catalyst and the light source claim limited to VCSEL, led, lamps but not solid state lasers.

SUMMARY

A novel method and apparatus is presented wherein an output of infra-red solid state laser or multiple of such lasers is quadrupled in frequency to obtain a laser output that emits energy in ultra violet C spectrum, and wherein this energy is then provided within an air duct as is normal in HVAC systems so as it kill pathogens that are airborne and being carried through the conduit. Further such a method reduces production of ozone, detrimental to human health and produced in other means of generating UVC and provides ease of control of such energy so as to maintain the required energy at a steady level for prolonged period of time.

The invention disclosed here and considered to be a preferred embodiment and which must be read as one particular implementation of this disclosure, without limitation of other embodiments, comprises an IR laser diode or diodes, emitting radiation at 1040 nm coupled to a solid state frequency doubler comprising a crystal and two mirrors, the output of which is 520 nm and a second frequency doubler comprising a crystal and two mirrors, the output of which is 260 nm. As the output needs not be a collimated beam, the crystals can be of poorer quality, thus reducing costs.

The output radiation is allowed to expand with a large angle of divergence against the normal practice of the art to have a highly collimated output.

It is clear to those familiar with the art that almost no ozone is created as there is no high level electromagnetic field present.

The radiation generating system is coupled to a detector that is then fed back to form a feedback loop that controls the output power and keeps it constant, increasing the current as the crystals age over time.

The whole apparatus is then contained inside of an HVAC conduit through which the medium to be treated passes. The insides of the conduit are covered with a reflective material such that the radiation reflects of the wall multiple times prior to being absorbed.

Multiple units may be used in a single HVAC conduit depending on the needs.

DETAILED DESCRIPTION

A preferred embodiment of this disclosure is presented here without limitation to other forms of implementing the solution described in the disclosure. These forms may vary the number of UVC Radiation Generators or their orientation.

A means of generating UVC through two stage frequency doubling is disclosed and will be well understood by persons with knowledge of the discipline. Standard methods of frequency doubling desire to produce a source of electromagnetic radiation that is collimated, thus requiring high quality optical components specifically the crystals that need to be without structural defects in the crystal lattice. These means incur a high cost. This unit in this disclosure that generates the UVC radiation is referred to as the UVC Radiation Generator.

This disclosure and the intent does not require collimated radiation, it requires the radiation to spread as wide as possible as the radiation needs to spread to cover the volume of the air duct in which the radiation source needs to be installed as further disclosed below. Therefore it will be understood that the lack of collimation means that the crystals do not have to be perfect and the optics can be chosen so that the cost is lower.

Figure 1:
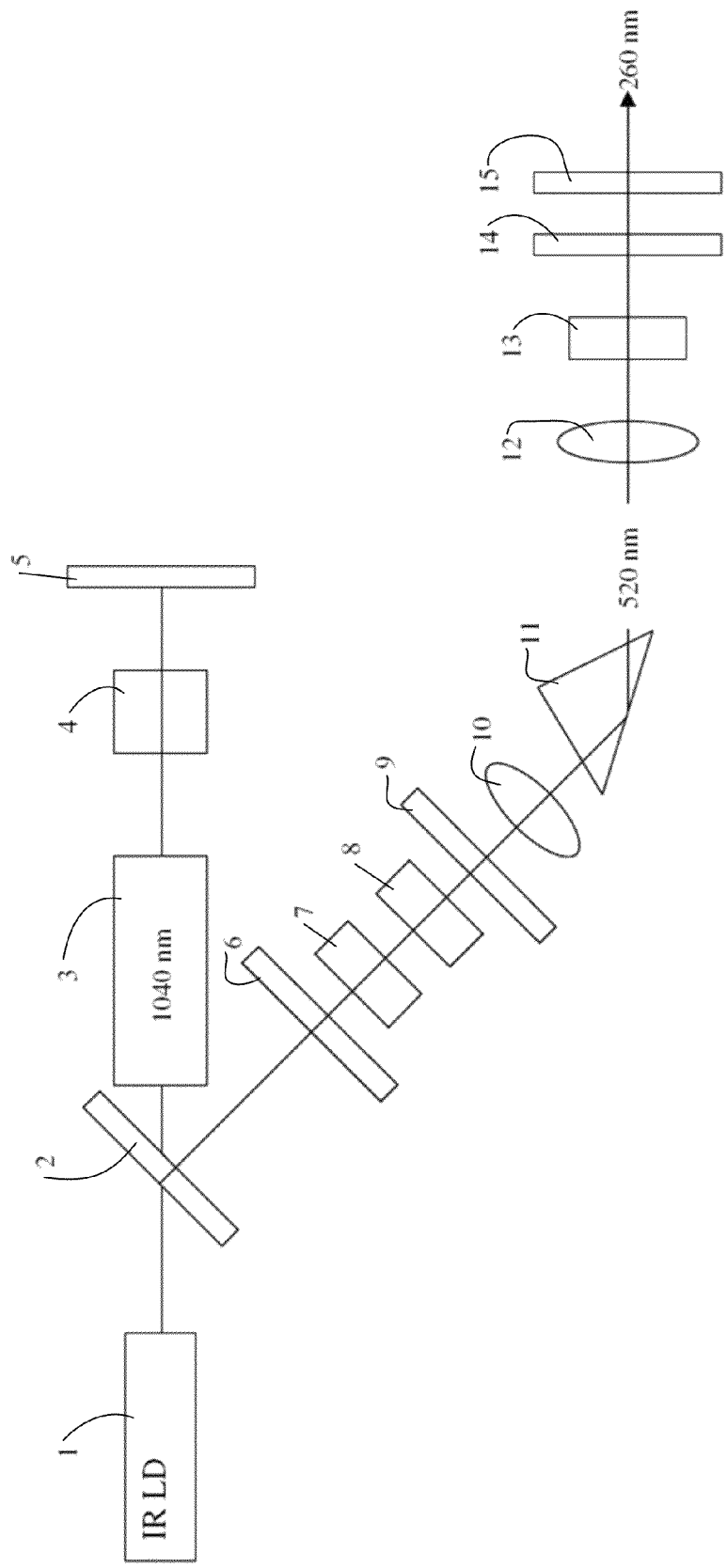
FIG. 1 shows a schematic of a two-stage quadruple harmonic generation of UVC from an IR source.

FIG. 1 shows an IR laser diode (LD) 1 acting as a pumping source and having an output beam directed to a mirror 2 positioned at an angle to the beam and that is highly reflective for the fundamental beam and transparent for the pumping beam. The beam from the IR laser diode 1 passes through the mirror 2 into a laser medium 3. The laser medium 3 can comprise Nd:YAG, Nd:YLF, Nd:YVO$_4$, Ti:Sapphire or other laser mediums, and operates at 1040 nm. The light passing through the laser medium 3 passes through a Q switch 4 and strikes mirror 5 that is highly reflective for the fundamental beam. The beam leaving laser medium 3 that strikes mirror 2 is reflected to a mirror 6 that is transparent for the fundamental beam and highly reflective to the harmonic beam generated in a first nonlinear medium, harmonic generation crystal 7 and a second nonlinear medium, harmonic generation crystal 8. Light leaving crystal 8 passes through a mirror 9, shaping optics 10 (lenses, mirrors or prisms), and an optical delay prism 11. Light at 520 nm leaves optical delay 11 passes through shaping optics, lenses, mirrors or prisms 12 into a third nonlinear medium, harmonic generation crystal 13, and exits to a mirror 14. Light passing through mirror 14 and an output device 15 that transmits a fourth harmonic beam is at a wavelength of 260 nm.

Figure 2:
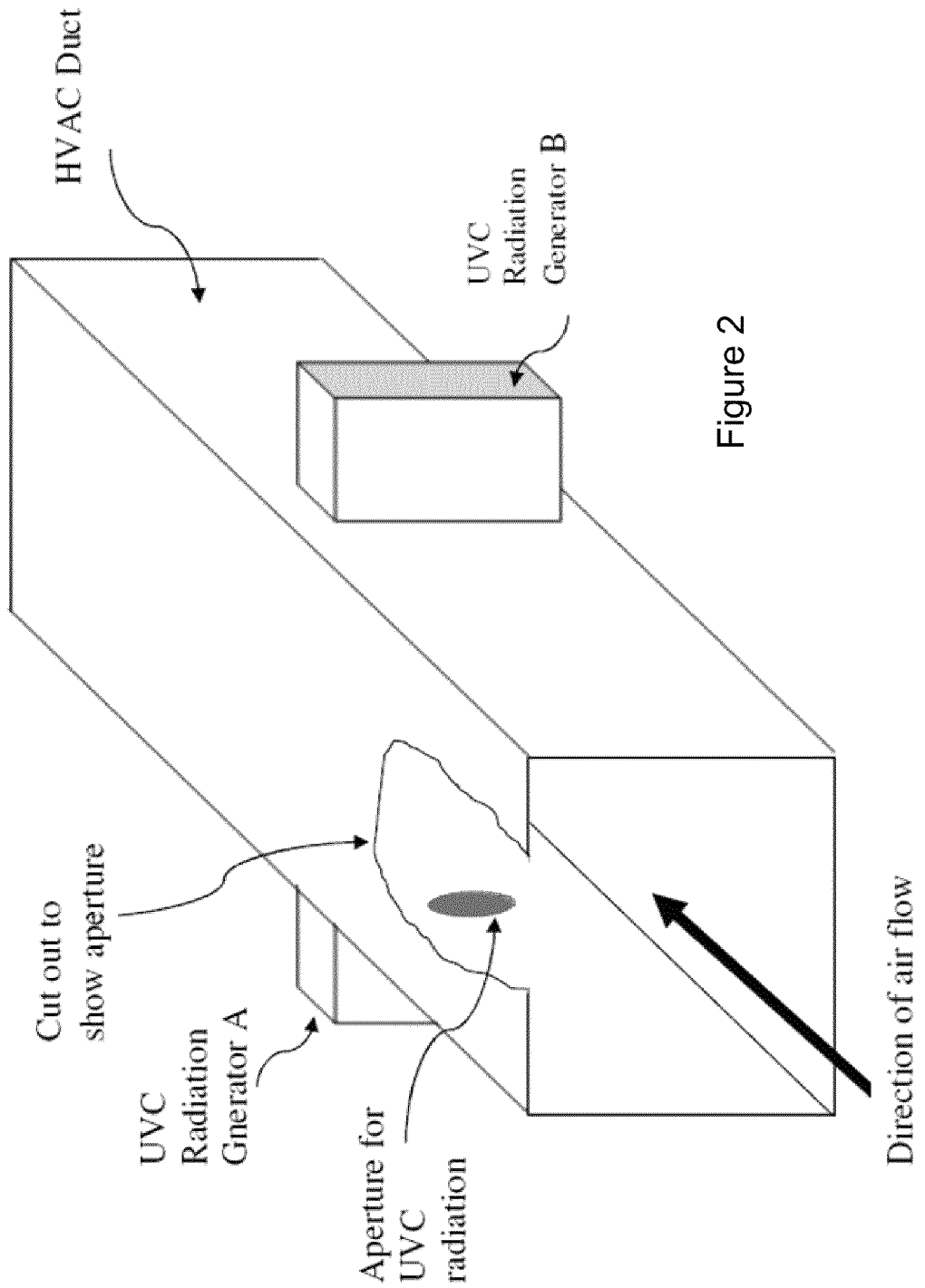
FIG. 2 shows a HVAC duct with two UVC Radiation Generators on each side of the duct. A cut out of the duct shows one of the opening through which the UVC radiation enters the duct. The air moves longitudinally through the duct.
Figure 3:
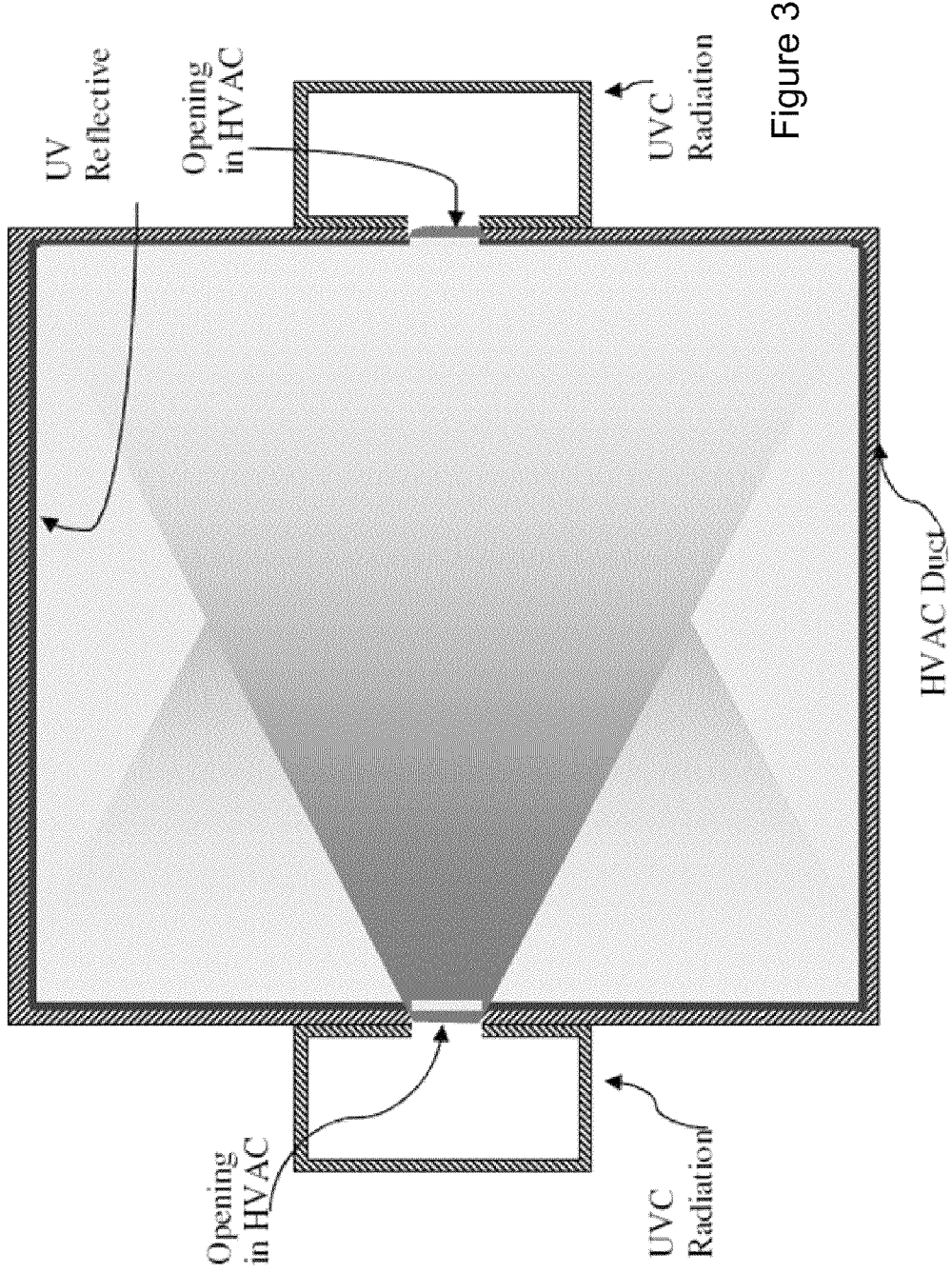
FIG. 3 shows how the radiation from the two UVC Radiation Generators fills the duct. The inner surfaces of the duct are coated with a UVC reflective material. The radiation reflects multiple times so as to fill the duct.

In the preferred embodiment, two such UVC Radiation Generators are installed in an HVAC conduit in opposition to each other, as is shown in FIG. 2, as well as the inner surface of the conduit are coated with a coating that is highly reflective of UVC radiation (FIG. 3). The resulting combination of the radiation pattern from the two UVC Radiation generators and the reflection from the inner surfaces of the HVAC duct provides sufficient energy in the duct so substantially all the pathogens being carried in the air are subject to 260 nm radiation. The resulting radiation in the duct is shown in FIG. 3.

There will be other arrangements wherein the number of UVC Radiation Generator may be more or less than two and may be placed in any other geometry as may be relevant to the desired level of energy exposure required.

Each of the two radiation sources has a sensor sensitive to UVC that is connected to a feedback control electronic circuit that controls the power of the excitation source in the UVC generator. Thus the radiation energy density is maintained through the operating life of the system and the elimination of the pathogens is predictable. This ensures that the effectiveness of the apparatus is predictable and thus reliable.

The UVC Radiation Generators radiating at 260 nm ensures that all the energy is applied to the destruction of the DNA of the pathogens, this attribute being an essential part of this disclosure.

What is claimed is:

1. An apparatus for killing airborne pathogens in an airflow comprising:
    an air duct;
    at least one UVC source mounted to a wall of said air duct, the UVC source comprising:
        an infrared laser; and
        a two stage frequency doubler configured to receive light from the infrared laser and output UVC light;
    wherein the infrared laser is configured to provide enough optical power to generate sufficient UVC in said air duct to kill said pathogens.

2. The apparatus as defined in claim 1, wherein the UVC source is in communication with said air duct and produces no ozone in said air duct.

3. The apparatus as defined in claim 1, wherein the two stage frequency doubler uses crystals having defects causing some divergence of light.

4. The apparatus as defined in claim 1, wherein the air duct is reflective to UVC light.

5. The apparatus as defined in claim 1, wherein said UVC source produces a wide angle beam in said duct.

6. The apparatus as defined in claim 5, wherein the air duct is reflective to UVC light.

7. The apparatus as defined in claim 6, wherein two said UVC sources are opposed to one another in said duct.

8. The apparatus as defined in claim 6, wherein the two stage frequency doubler uses crystals having defects causing some divergence of light.

9. The apparatus as defined in claim 1, wherein two said UVC sources are opposed to one another in said duct.

* * * * *